United States Patent [19]
Adrian

[11] 4,387,993
[45] Jun. 14, 1983

[54] PARTICLE SIZE MEASURING METHOD AND APPARATUS

[75] Inventor: Ronald J. Adrian, Champaign, Ill.

[73] Assignee: TSI Incorporated, St. Paul, Minn.

[21] Appl. No.: 277,150

[22] Filed: Jun. 25, 1981

[51] Int. Cl.³ .............................................. G01N 15/02
[52] U.S. Cl. ...................................... 356/336; 356/28
[58] Field of Search ................. 356/28, 28.5, 336, 349

[56] References Cited

U.S. PATENT DOCUMENTS

| | | | |
|---|---|---|---|
| 3,532,427 | 10/1970 | Paine | 356/28 |
| 3,548,655 | 12/1970 | Rudd | 73/194 |
| 3,941,477 | 3/1976 | Schodl | 356/28 |
| 4,140,395 | 2/1979 | Kreikebaum | 356/336 |
| 4,348,111 | 9/1982 | Goulas et al. | 356/336 |

OTHER PUBLICATIONS

"Simultaneous Velocity and Particle Size Measurements in Two Phase Flows by Laser Anemometry", A. Ungut, A. J. Yule, D. S. Taylor and N. A. Chigier, University of Sheffield, Sheffield, England, AIAA 16th Aerospace Sciences Meeting, Huntsville, AL, Jan. 16–18, 1978.

*Primary Examiner*—John K. Corbin
*Assistant Examiner*—Matthew W. Koren
*Attorney, Agent, or Firm*—Burd, Bartz & Gutenkauf

[57] ABSTRACT

A particle size measuring apparatus and method has a laser unit and optics that provide a central focused light area surrounded by an annular focused light area. Particles moving with fluid through the center of central focus light area cause the light to scatter. The scattered light is sensed and converted to readable signals indicative of particle size.

26 Claims, 6 Drawing Figures

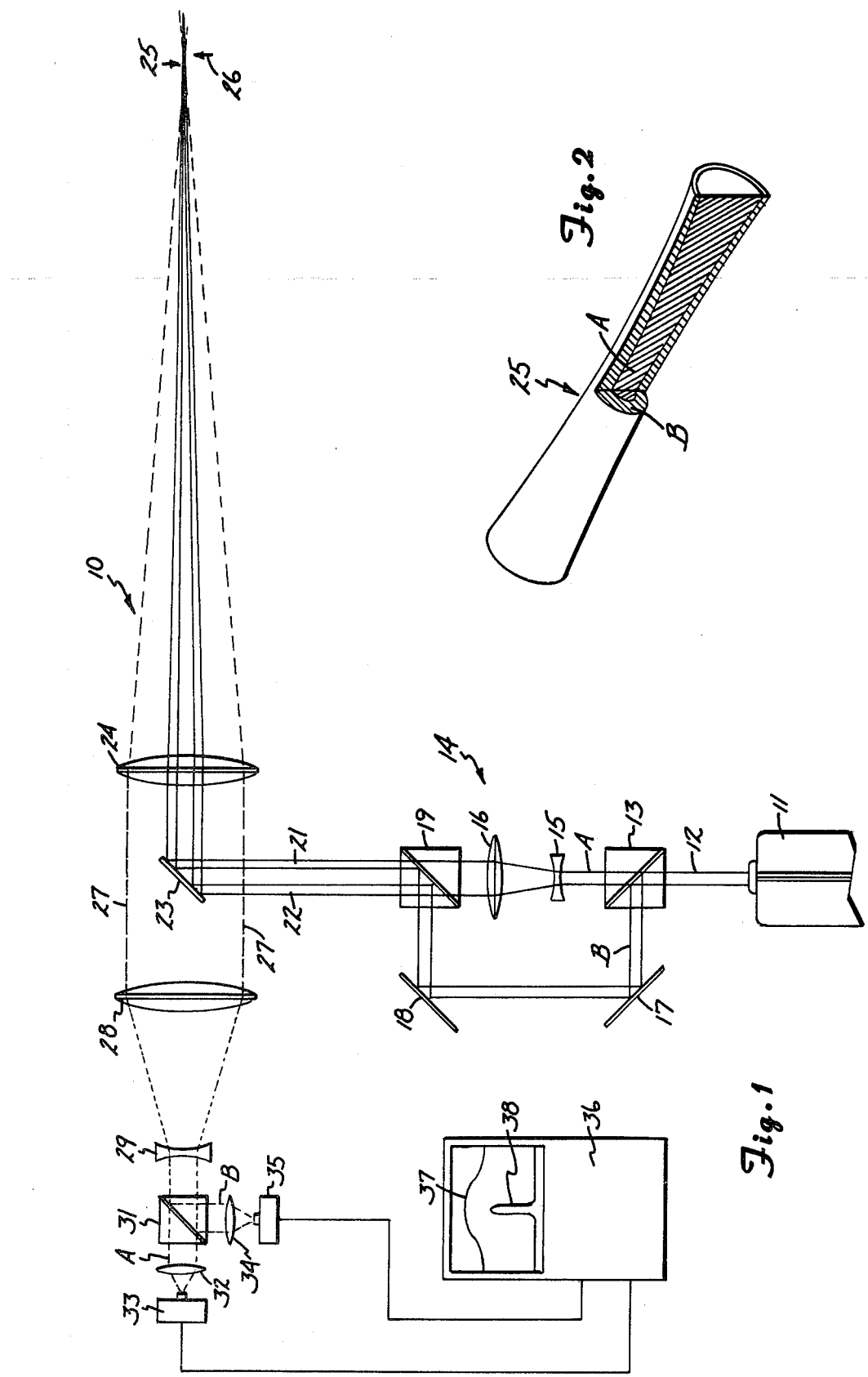

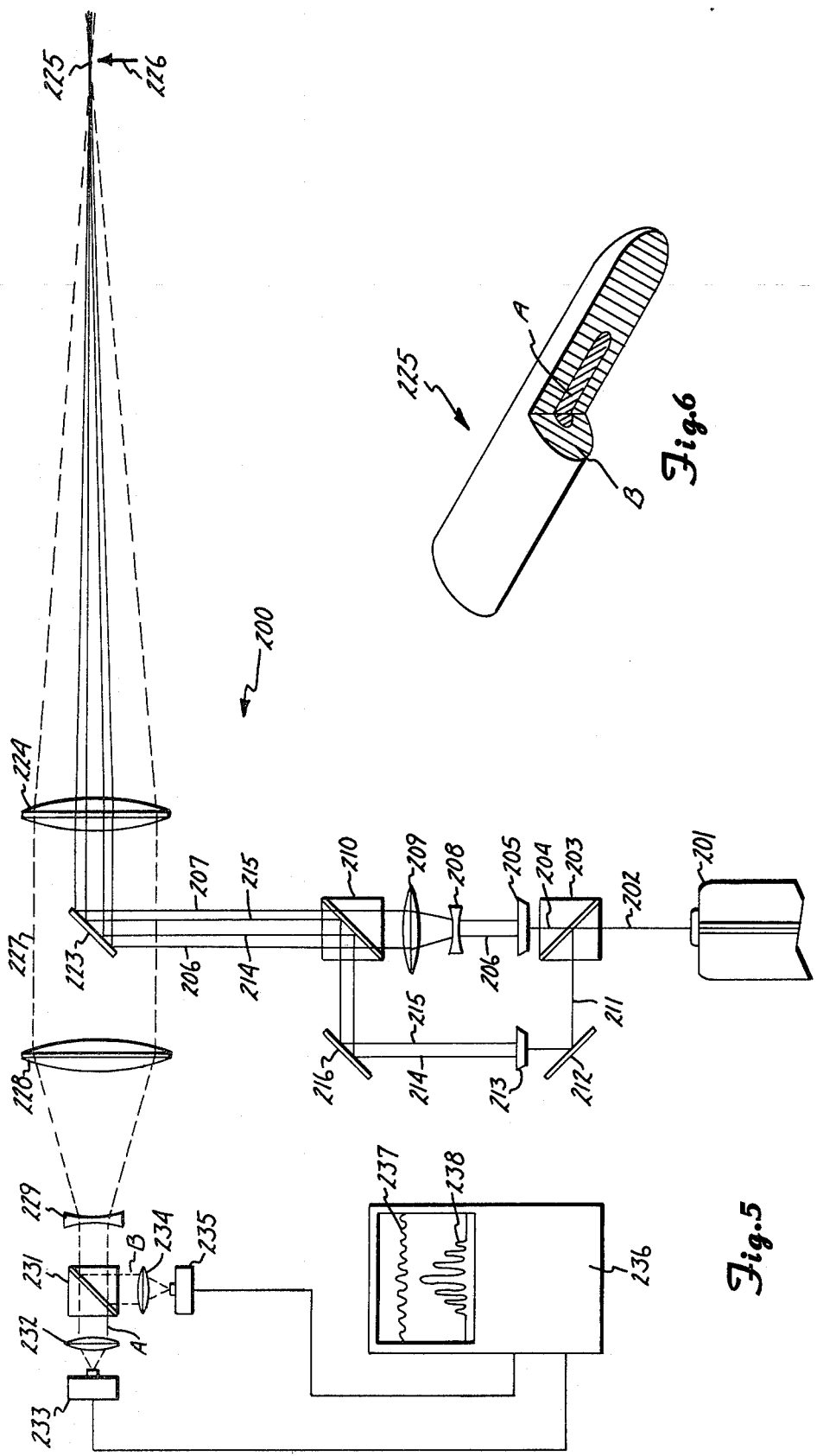

PARTICLE SIZE MEASURING METHOD AND APPARATUS

SUMMARY OF INVENTION

The invention relates to a method and apparatus that uses a laser light source to measure particle characteristics, such as the velocity and size of particles moving with a fluid. The measurement is made without disturbing the fluid. The laser light source generates a light beam that is separated into a plurality of separate colinear light beams. Optics function to focus the colinear light beams in a common focus area. The focus area has two concentric measuring means. The measuring means include a small central focused light area surrounded by a larger annular focused light area. Particles moving with fluid through the center of the focus area are sensed in the small light area to determine particle flow through the large light area. The particles moving through the light cause the focused light to scatter. The scattered light is sensed and converted to readable signals indicative of particle characteristics, as size and velocity.

The apparatus comprises a laser unit operable to generate collimated light beams having a plurality of separate components, as separate colors. A first means separates the light beam into a plurality of separate light beams and arranges the separate light beams in relative colinear relationship. Focusing lens means focuses the colinear related plurality of light beams in a common focus area. The focusing area has concentrically positioned focused light. The fluid and particles move through the focused light. The particles moving through the center of the focused light scatter the light. Optical means are located in a position to collect and focus the scattered light on a means for separating the scattered light into a plurality of scattered light beams. Photodetector means sense each of the separate plurality of scattered light means and produce electrical signals corresponding to the amount of sensed light. The electrical signals from the photodetector means are received by means which produce readable information as to movement of particles through the center of the focused light and information related to the characteristics of the particles, such as particle size and velocity, moving with the fluid through the focused light.

The first means includes color splitter means that cooperate with lens means to divide the light beams from the laser unit into separate colored light beams and colinearly align the separate light beams. A mirror optically aligned with the focusing lens means reflects the colinearly aligned separate light beams to the focusing lens means. Optical means collect the scattered light resulting from a particle moving through the focused light. The focusing lens is part of the optical means used to collect the scattered light whereby the focused light and scattered light have the same optical axis. The focusing optical axis is generally normal to the optical axis of the separate colinear light beams. The mirror means is smaller than the focusing lens means whereby the scattered light collected by the focusing lens passes around the mirror means. The collection of scattered light only around the mirror means and focusing the scattered light on the photodetector means limits the length of the focused light volume sensed by the photodetector means.

The focusing of the separate light beams in a focused area identifies a path through the center of the focused area making the scattered light intensity meaningful. The second light beam identifies the center of the focus area. The particles moving through the center of the focus area are the particles that are subjected to measurement. It is advantageous to make measurements only on particles that go through a certain area of a laser beam. This isolates the measurement to a definite spot in the field and isolates measurement relative to the laser beam itself. An example would be an application where the analysis depended on all particles passing through the same intensity distribution of laser light.

IN THE DRAWINGS

FIG. 1 shows a first laser particle measurement apparatus of the invention;

FIG. 2 is an enlarged perspective view, partly sectioned, of the focus area of the light beams generated by the apparatus of FIG. 1;

FIG. 5 is a third laser particle measurement apparatus of the invention; and

FIG. 6 is an enlarged perspective view, partly sectioned, of the focus area of the light beams of the apparatus of FIG. 5.

DESCRIPTION OF PREFERRED EMBODIMENTS

Figures 3, 4:
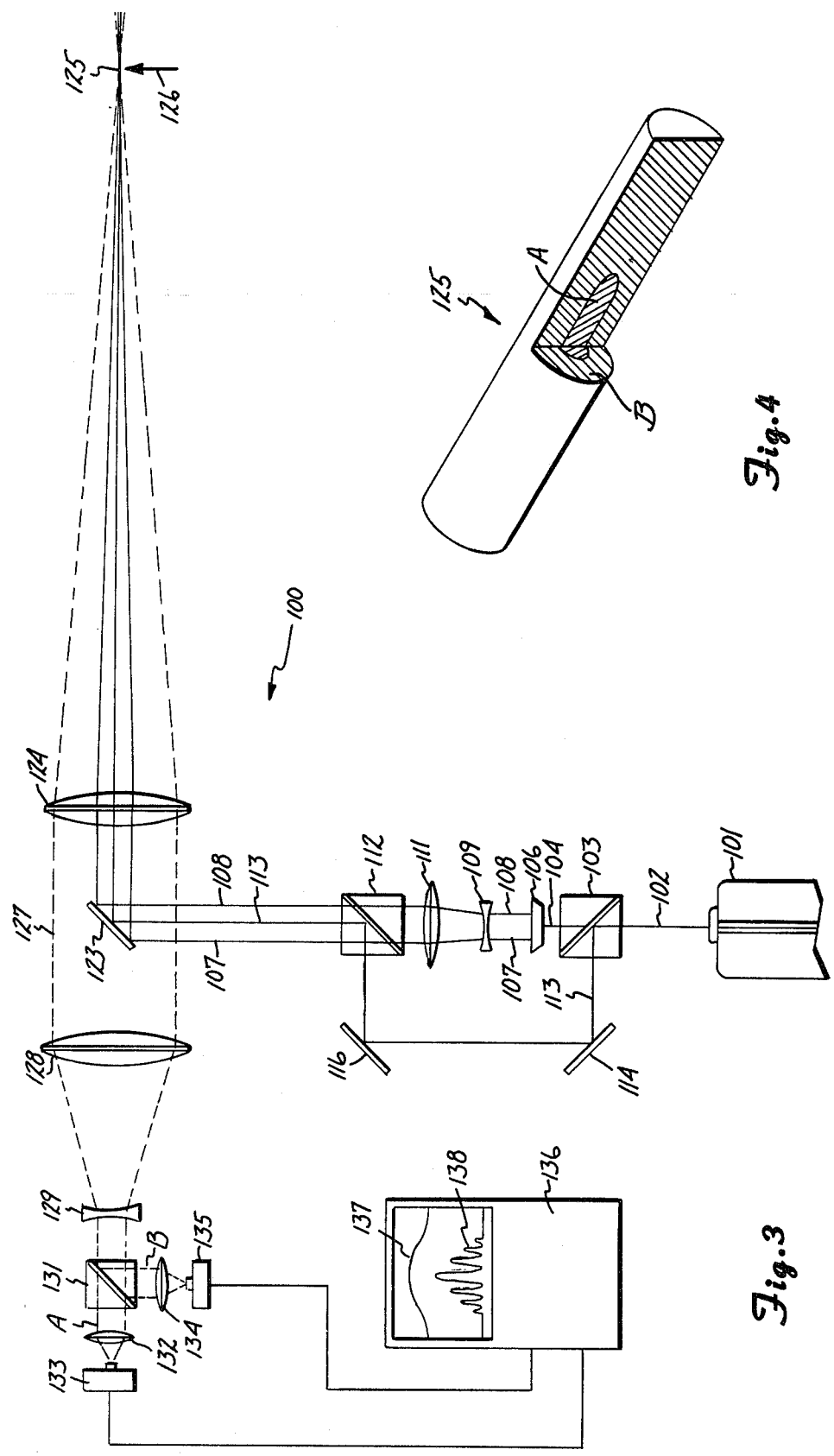
FIG. 3 is a second laser particle measurement apparatus of the invention.
FIG. 4 is an enlarged perspective view, partly sectioned, of the focus area of the light beams of the apparatus of FIG. 3.

Referring to FIG. 1, there is shown a laser particle measurement apparatus indicated generally at 10 for measuring particle size and velocimetry in situ in a moving fluid without disturbing the fluid. Apparatus 10 is a two light beam system without interference fringes. Apparatus 10 has a laser unit 11 operable to generate a collimated light beam 12 having at least two components, as colors indicated as A and B light. For example, laser unit 11 can be an Argon-ion laser with 488 nm and 514.5 nm. A color splitter 13 transmits one or color A light and reflects the other or color B light. A light beam expander indicated generally at 14 increases the diameter of the beam of color A light. Beam expander 14 has a negative lens 15 receiving color A light from splitter 13 and a positive lens 16 aligned with lens 15. A pair of mirrors 17 and 18 direct B light to a second color splitter 19. A and B lights are directed to color splitter 19 where A light is transmitted and B light is reflected to form colinear light beams 21 and 22. Light beams 21 and 22 have different diameters and are located along the same longitudinal center line.

A mirror 23 directs light beams 21 and 22 through a lens 24 which focuses both A and B light at a common focus area 25. The diameter of the light beam at the focal point or area 25 is inversely proportional to the diameter of the light beam entering lens 24. For a small focal diameter, the light beam entering lens 24 must be large. In apparatus 10, the diameter of the light beam at the focus area 25 is small compared to the length scale of velocity change so that a particle always moves along a straight line when traversing the center of the focus area. The focused A and B light beams have a Gaussian intensity distribution. Mirror 23 is smaller than lens 24 and is located along the longitudinal center line of lens 24 to allow scattered light to by-pass mirror 23. Mirror 23 also locates the axis of the colinear light beams normal to the optical focusing axis.

A particle 26 moving through focus area 25 will scatter the focused light. The scattered light indicated by broken lines 27 is collected by lens 24. The scattered light 27 that passes around mirror 23 is focused and re-collimated by positive lens 28 and negative lens 29. A third color splitter 31 reflects scattered B light and transmits scattered A light. Lens 32 focuses B light onto a photodetector 33. A lens 34 focuses A light onto photodetector 35. The light directed to photodetectors 33 and 35 activates the photodetectors which produce electrical output signals representing the amount of light focused on the photodetectors 33 and 35. This light is representative of the size of the particles and velocity of the particles moving through focus area 25. The output signals of the photodetectors 33 and 35 for a particle flowing through the measuring or focus area 25 are visually displayed on an oscilloscope 36 as separate traces 37 and 38. If there are two or more light colors present, the two light colors of interest can be selected using appropriate optical filters in front of photodetectors 33 and 35.

FIG. 2 shows an enlarged perspective view of the light beam focus area 25 for A and B color light. The A and B light is focused along a common longitudinal axis. A light beam focuses centrally of B light beam and is used to identify particles moving through the center of the focus area 25. B light beam surrounds and forms a sleeve around the focus area of A light beam. B light beam is used to view particles that see substantially the same light intensity distribution as they traverse focus area 25.

The length of the volume seen by photodetector 31 is limited to focus area 25, since only the scattered light around mirror 23 is focused on the photodetector. The focusing and collecting optics are located on one side of the focus area. Lens 24 functions as the focusing and collecting optic. The collecting optics need not use the same lens as the focusing optics. Also, the collecting optics can be placed at any convenient location or at a location that produces optimum signal properties.

Apparatus 10 can be adapted to use a single color light by utilizing the polarization properties of light to separate the signals. Color splitters 13 and 19 are replaced with polarization rotators. Laser unit 11 generates a light beam with the polarization of the light orientated relative to the polarization rotators.

Referring to FIG. 3, there is shown a modification of the laser particle measurement apparatus indicated generally at 100 operable to measure in situ particle size and particle velocity in a moving fluid without disturbing or disarranging the fluid. Apparatus 100 has a laser unit 101 operable to generate collimated light beam 102 having at least two colors, indicated as A and B light beams. A first light beam splitter 103 transmits color A light beam to a light beam expander 106 which divides the light beam into separate beams 107 and 108. Light beams 107 and 108 are directed to a negative lens 109 located adjacent a positive lens 111. The light beams are directed by lens 111 to a second beam splitter 112. A mirror 123 reflects light beams 107 and 108 from splitter 112 through a focusing lens 124. The light beams 107 and 108 are focused by lens 124 in a common focus area or focal point 125.

Beam splitter 103 reflects color B light beam 113. Mirrors 114 and 116 direct light beam 113 to the center of the second color splitter 112. The beam 113 is directed by the second splitter 112 to mirror 123. From mirror 123 beam 113 passes through the optical axis of lens 124 and passes through the longitudinal axis of focal point 125. Mirror 123 is smaller in diameter than lens 124 and is located along the longitudinal center line or optical axis of lens 124. This allows the scattered light, indicated by the broken lines 127, to by-pass mirror 123. Mirror 123 also locates the axis of the colinear light beams normal to the optical focusing axis.

A particle 126 moving through focus area 125 will scatter the focused light. The scattered light indicated by broken lines 127 is collected by lens 124. The scattered light 127 that passes around mirror 123 is focused and re-collimated by positive lens 128. A negative lens 129 aligned with lens 128 directs the light to a third color splitter 131. Splitter 131 reflects scattered B light and transmits scattered A light. Lens 132 focuses the B light on a photodetector 133. Lens 134 focuses the A scattered light onto photodetector 135. Photodetectors 133 and 135 are electrically coupled with lines to an oscilloscope 136. The output signals 137 and 138 of the oscilloscope represent the output signals of photodetectors 133 and 135. The signal or trace 137 is a function of the B colored light detected by photodetector 135. The trace 138 is a signal that receives a frequency due to the intensity variations caused by the interference of light beams. The frequency of signal 138 is a direct measure of particle velocity moving through the center of the focus area 125. The length of the measurement of focus area 125 is restricted by the light beam crossing area, rather than by light collecting objects.

The focus area 125 is shown in detail in FIG. 4. For light beam A, the only portion in detail is the region where the two beams 107 and 108 cross to form an interference pattern. The focus area 125 is restricted by the light beam crossing area, rather than by the collecting optics. The light beam B in the focus area 125 surrounds the crossing light beams A.

Referring to FIGS. 5 and 6, there is shown another modification of the laser particle measurement apparatus indicated generally at 200. Apparatus 200 functions to measure particle size and particle velocity insitu without disturbing the fluid. Apparatus 200 has a laser unit 201 operable to generate a collimated light beam 202 having at least two colors, such as color A light beam and color B light beam. A beam splitter 203 separates light beam 202 into a first light beam 204 and a second light beam 211. A beam expander 205 divides beam 204 into separate light beams 206 and 207. A negative lens 208 expands beams 206 and 207 and directs the beams to a lens 209. The light beams 206 and 207 pass through a second color splitter 210 onto a mirror 223. The mirror 223 reflects the light beams 206 and 207 through a focusing lens 224. The light beams 206 and 207 cross at focus area 225. In other words, lens 224 focuses the light beams 206 and 207 in focus area 225.

The light beam 211 is reflected with a mirror 212 through a second beam expander 213. Expander 213 divides light beam 211 into separate light beams 214 and 215 which are reflected with mirror 216 to beam splitter 210. The light beams 214 and 215 are directed by beam splitter 210 to mirror 223 which reflects the light beams 214 and 215 through lens 224 to focus area 225. The light beams 214 and 215 are located between light beams 206 and 207 and cross at the focus area 225.

A detail of focus area 225 is shown in FIG. 6. The focus area 225 has a shape of two concentrical ellipsoids. Lens 224 focuses and crosses the four collimated light beams in focus area 225. The light beams 206, 207, 214, and 215 are focused in the area that is defined as the region where the intensity variation of the interference fringes is greater than the center line light intensity.

The resulting signals for a particle 226 passing through the center of the focus area 225 is shown on the oscilloscope 226 as traces 237 and 238. A particle 226 moving through focus area 225 produces scattered light indicated by the dotted lines 227. The scattered light 227 is collected by lens 224. The collected light that passes around lens 223 is directed by lens 228 to a negative lens 229 located in optical alignment with a third color splitter 231. Color splitter 231 directs scattered B light to lens 234 in alignment with a photodetector 235. Photodetector 235 is electrically coupled to an oscilloscope 236 so that the output signal of photodetector 235 results in a trace 237 on oscilloscope 236.

The A light beam passing through third color splitter 231 is directed by lens 232 to a second photodetector 233. Photodetector 233 is electrically coupled to oscilloscope 236 so that the output signal of photodetector 233 results in an oscilloscope trace 238.

Apparatus 200 is useable in situations where two distinct size distributions of particles are present. The velocity of small particles follows the fluid flow. The signal or trace 237 from the A light beam would be used only to verify that a measurement should be made using the B light beams. The amplitude of the trace 238 is a measure of particle size. Trace 238 is a signal showing the amount of light scattered by a particle moving through the center of the focus area. It is proportional to particle size. The frequency of trace 238 is the measure of the velocity of the large particles. The total system measures fluid velocity, as well as large particle size and velocity.

While there are shown and described several embodiments of the apparatus and method of measuring particle velocity and size in a fluid, it is understood that changes in the structure, laser unit, optics and arrangement of structure and optics can be made by one skilled in the art without departing from the invention. The method and apparatus uses at least two recognized light beams to measure particle velocity and particle size. The light beams can have different colors or different polarization. Two laser units having output light beams of different wave lengths can be used. The invention is defined in the following claims.

The embodiments of the invention in which an exclusive property or privilege is claimed are defined as follows:

1. An apparatus for measuring particle size of particles moving with a fluid comprising: a laser unit operable to generate a collimated light beam, first means for separating the light beam into a plurality of separate different light beams and arranging the light beams in relative colinear relationship, said first means including means to expand one of said light beams to provide an expanded first light beam, and a second light beam, and means to colinearly arrange the expanded first light beam with said second light beam, lens means to focus the colinearly related first and second light beams in a common focus area having concentrically positioned focused light, said fluid and particles moving through the center of said focus area whereby the particles moving through the focus area scatter light, means to collect and recollimate the scattered light, means for separating the collected scattered light into a plurality of scattered light beams, photodetector means for sensing the separate plurality of scattered light beams and producing electrical signals corresponding to the amount of sensed light, and means for receiving said electrical signals and producing readable information as to the size of the particles moving with the fluid through the focus area.

2. The apparatus of claim 1 wherein: the collimated light beam generated by the laser unit has a plurality of colors, said first means includes color splitter means for separating the light beam into a plurality of separate different color light beams.

3. The apparatus of claim 1 including: mirror means optically aligned with the second lens means to reflect the colinearly related light beams toward the second lens means, said mirror means being smaller than said second lens means whereby said scattered light passes around the mirror means.

4. The apparatus of claim 3 wherein: the first means has an optical axis located generally normal to the optical axis of the second lens means.

5. The apparatus of claim 1 wherein: the first means includes means to separate the light beam into separate polarized light beams.

6. The apparatus of claim 1 wherein: the means to collect the scattered light includes the lens means.

7. The apparatus of claim 1 wherein: the collimated light beam generated by the laser unit has a plurality of colors, said first means includes a first color splitter, lens means to expand the first light beam transmitted through the first color splitter, and a second color splitter to colinearly arrange the first light beam with said second light beam.

8. An apparatus for measuring the size of particles moving with a fluid comprising: a laser unit operable to generate a collimated light beam having at least two colors, first means for dividing the light beam into a first color light beam and a second color light beam, second means to expand the first light beam, third means to direct the second light beam parallel to the first light beam to provide colinear first and second light beams, first lens means to focus the colinear first and second light beams in a common focus area having concentrically positioned focused light, said fluid and particles moving through said focus area whereby the particles moving through the center of the focus area scatter light, fourth means to collect the scattered light, fifth means for dividing the collected scattered light into a first scattered light beam and a second scattered light beam, first light sensing means for sensing the first scattered light beam and producing an electrical signal corresponding to the amount of light sensed by the first light sensing means, second light sensing means for sensing the second scattered light beam and producing an electrical signal corresponding to the amount of light sensed by the second light sensing means, and sixth means for receiving said electrical signals and producing readable information as to the size of particles moving with the fluid through the focus area.

9. The apparatus of claim 8 including: a mirror located adjacent the lens means reflects the colinear first and second light beams toward the lens means, said mirror being smaller than the lens means and optically aligned therewith whereby scattered light passes around the mirror.

10. The apparatus of claim 9 wherein: the lens means and fourth means include a common lens.

11. The apparatus of claim 8 wherein: the first means comprises a first color splitter, the second means is a second lens means operable to expand the first light beam, and the third means is a second color splitter which forms colinear first and second light beams.

12. The apparatus of claim 8 wherein: the first lens means and fourth means include a common lens.

13. The apparatus of claim 12 including: a mirror optically aligned with the common lens to reflect the colinear first and second light beams toward said common lens, said mirror being smaller than said common lens, said scattered light being collectd by said common lens and passing around the mirror.

14. The apparatus of claim 12 wherein: the common lens focuses the first light beam around the second light beam in the focus area.

15. The apparatus of claim 8 wherein: the first means comprises a color splitter which transmits the first light beam and reflects the second light beam, the second means includes second lens means operable to expand the first light beam, and the third means includes a second color splitter which reflects the second light beam and transmits the first light beam to form the colinear first and second light beams, said first and second color splitters and second lens means being optically aligned along the optical axis of the colinear first and second light beams.

16. The apparatus of claim 15 wherein: said optical axis is generally normal to the optical axis of the first lens means which focuses the first and second light beams in the common focus area.

17. The apparatus of claim 16 including: mirror means optically aligned with the first lens means to reflect the colinear first and second light beams toward the first lens means, said mirror means being smaller than said first lens means whereby scattered light passes around the mirror means.

18. The apparatus of claim 17 wherein: the first lens means and fourth means include a common lens optically aligned with the mirror means.

19. The method of measuring the size of particles moving with a fluid comprising: generating a laser light beam, separating the laser light beam into at least first and second different color light beams, expanding the first light beam, arranging the expanded first light beam and second light beam in relative colinear relationship to provide colinear separate light beams, focusing the two colinear first and second light beams in a common focus area having concentrically positioned focused light, moving fluid and particles therein transversely through the center of the focus area whereby said particles scatter light, collecting the scattered light, separating the collected scattered light into two light beams corresponding to the first and second light beams, sensing the two light beams, and producing electrical output signals related to the sensed two light beams, and converting said electrical output signals to readable information as to the size of the particles moving with the fluid through the focus area.

20. The method of claim 19 wherein: the light beam is separated into a plurality of light beams, said plurality light beams being focused in the focus area, at least two of said plurality of light beams being crossed in the focus area, said scattered light being collected and separated into light beams corresponding to the plurality of light beams, said scattered light being separately sensed to produce separate electrical output signals, each of said output signals being connected to readable information related to the velocity of particles and size of large particles moving through the focus area.

21. The method of claim 19 wherein: the scattered light is collected with lens means for focusing the colinear light beams in the focus area.

22. The method of measuring particle characteristics of particles moving with a fluid comprising: generating a laser light beam, separating the light beam into a plurality of separate light beams, expanding one of said separated light beams, to provide an expanded light beam and a non-expanded light beam, arranging the expanded light beam and non-expanded light beam in relative colinear relationship to provide colinear separate light beams, focusing the colinear separate light beams in a common focus area having concentrically positioned focused light, moving particles through the focus area whereby said particles scatter light, collecting the scattered light, separating the collected scattered light into a plurality of scattered light beams, sensing the plurality of scattered light beams, producing output signals related to the sensed scattered light beams, and converting said output signals to readable information as to particle characteristics of particles moving through the focus area.

23. The method of claim 22 wherein: the light beam is separated into separate polarized light beams.

24. The method of claim 22 wherein: the light beam is separated into different color light beams.

25. The method of claim 22 wherein: the light beam is separated into two different color light beams, said light beams being focused in the common focus area, said scattered light being collected and separated into two light beams corresponding to the two different color light beams, said collected scattered light being separately sensed to produce separate output signals, each of said output signals being converted to readable information related to the size and velocity of particles moving through the focus area.

26. The method of claim 22 wherein: the scattered light is collected with lens means for focusing the colinear separate light beams in the common focus area.

* * * * *